United States Patent
Che et al.

(10) Patent No.: US 9,238,659 B2
(45) Date of Patent: Jan. 19, 2016

(54) METHOD OF USING BINUCLEAR GOLD (I) COMPOUNDS FOR CANCER TREATMENT

(71) Applicant: University of Hong Kong, Hong Kong (CN)

(72) Inventors: Chi Ming Che, Hong Kong (CN); Taotao Zou, Hong Kong (CN)

(73) Assignee: THE UNIVERSITY OF HONG KONG, Hong Kong (CN)

(*) Notice: Subject to any disclaimer, the term of this patent is extended or adjusted under 35 U.S.C. 154(b) by 59 days.

(21) Appl. No.: 14/070,096

(22) Filed: Nov. 1, 2013

(65) Prior Publication Data

US 2014/0142065 A1  May 22, 2014

Related U.S. Application Data

(60) Provisional application No. 61/727,972, filed on Nov. 19, 2012.

(51) Int. Cl.
| | |
|---|---|
| *A61K 31/28* | (2006.01) |
| *C07F 1/00* | (2006.01) |
| *C07F 9/50* | (2006.01) |
| *C07F 9/6558* | (2006.01) |
| *C07F 1/12* | (2006.01) |

(52) U.S. Cl.
CPC . *C07F 1/00* (2013.01); *A61K 31/28* (2013.01); *C07F 1/005* (2013.01); *C07F 1/12* (2013.01); *C07F 9/5045* (2013.01); *C07F 9/65583* (2013.01)

(58) Field of Classification Search
CPC .................................................. A61K 31/28
See application file for complete search history.

(56) References Cited

U.S. PATENT DOCUMENTS

2003/0114695 A1* 6/2003 Leung ................. C07F 9/6596
556/12
2007/0142336 A1* 6/2007 Flower .................. A61K 31/66
514/102

OTHER PUBLICATIONS

Wong, E. et al. *Chem. Rev.* 1999, 99, 2451.
Sadler, P. J. et al. *J. Am. Chem. Soc.* 2002, 124, 3064.
Sadler, P. J. Curr. Opin. *Chem. Biol.* 2008, 12, 197.
Berners-Price, S. J. (2011) Gold-Based Therapeutic Agents: A New Perspective, in Bioinorganic Medicinal Chemistry (ed E. Alessio), Wiley-VCH Verlag GmbH & Co. KGaA, Weinheim, Germany. doi:10.1002/9783527633104.ch7.
Christopher et al. *Cancer Res.* 1985, 45, 32.
Berners-Price, S. J. et al. *Cancer Res.* 1986, 46, 5486.
Berners-Price, S. J.; Filipovska, A. Metallomics 2011, 3, 863.
Berners-Price, S. J. et al. *Dalton Trans* 2007, 4943.
Che, C. -M. et al. *Angew. Chem. Int. Ed.* 1999, 38, 2783.
Che, C. -M. et al. *J. Am. Chem. Soc.* 1999, 121, 4799.
Che, C.-M. et al. *Chem. Commun.* 2011, 47, 9318.
Che, C.-M. et al. *Chem. Commun.* 2010, 46, 3893.
Che, C.-M. et al. *Chem. Sci.* 2011, 2, 728.
Berners-Price, S. J.; Filipovska, A. et al. *J. Am. Chem. Soc.* 2008, 130, 12570.
Fregona, D. et al. *Int. J. Cancer.* 2011, 129, 487.

* cited by examiner

*Primary Examiner* — Wu-Cheng Winston Shen
*Assistant Examiner* — Christopher R Stone
(74) *Attorney, Agent, or Firm* — Leason Ellis LLP.

(57) ABSTRACT

Provided herein is a method of treating cancer by the administration of binuclear gold(I) compounds in patients in need thereof. The pharmaceutical compounds possess anti-cancer activity such as the induction of cell death, inhibition of cellular proliferation, inhibition of thioredoxin reductase activity, and inhibition of tumor growth in vivo.

7 Claims, 10 Drawing Sheets

Solvent control    5 mg/kg of 1

METHOD OF USING BINUCLEAR GOLD (I) COMPOUNDS FOR CANCER TREATMENT

RELATED APPLICATION

Figure 1:
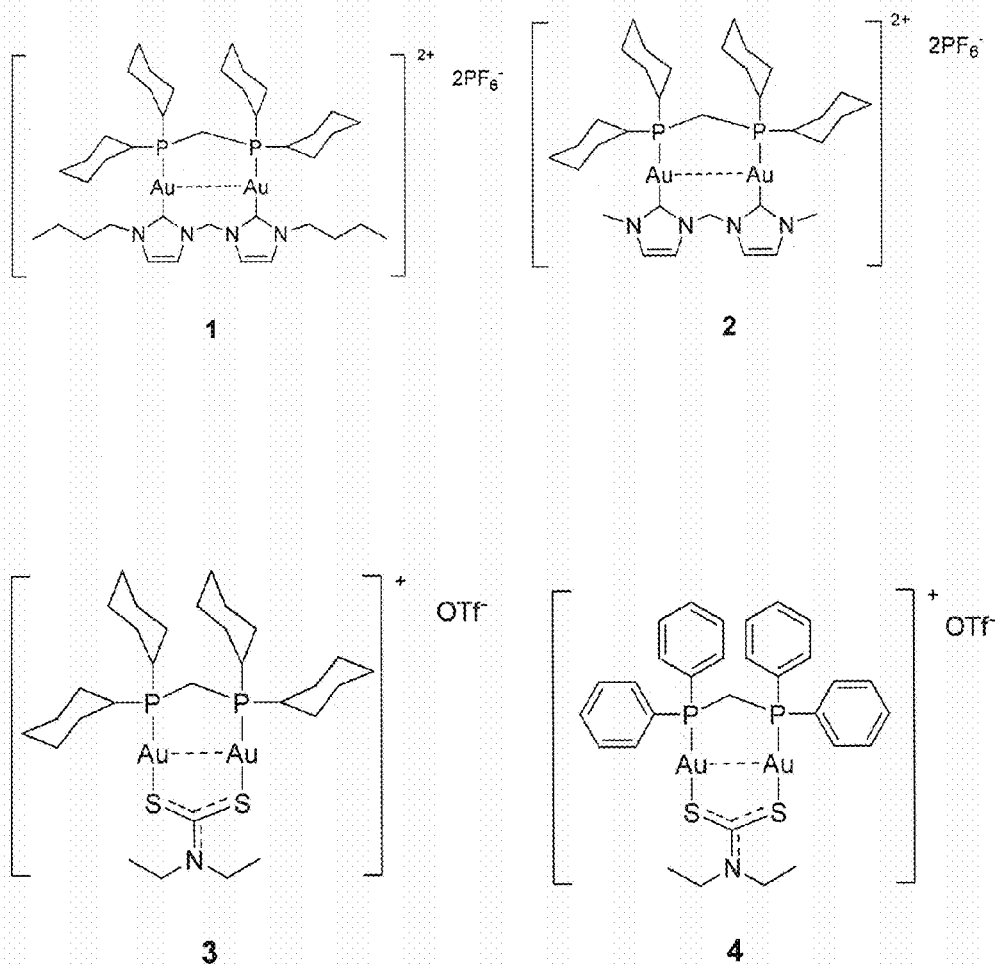
Figure 1:
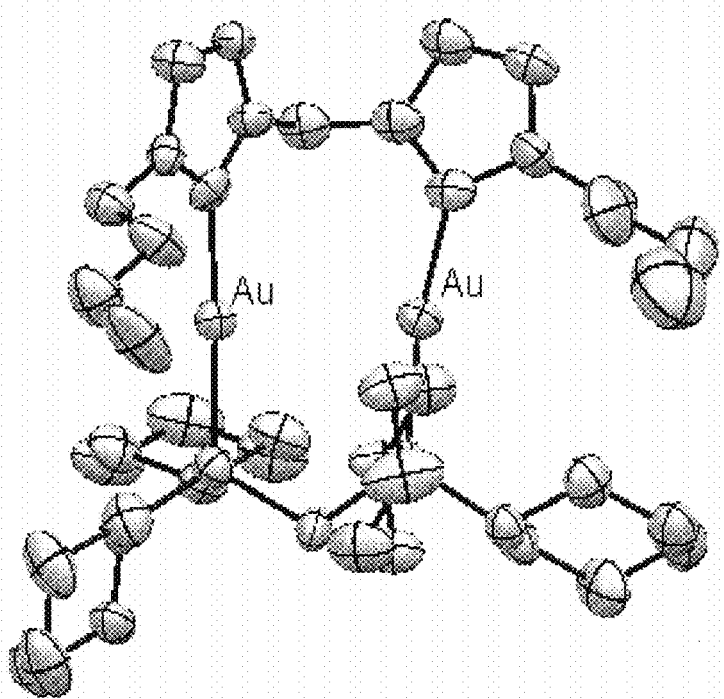

This application claims the benefit of U.S. provisional application Ser. No. 61/727,972, filed Nov. 19, 2012, which is hereby incorporated by reference in its entirety.

1. INTRODUCTION

The invention generally relates to a method of treating cancer by the administration of a binuclear gold(I) compound. In certain embodiments, the methods of treating and preventing cancer or tumor are in combination with other cancer or tumor treatment. In certain embodiments, the cancer or tumor treatment is chemotherapy, radiation therapy, gene therapy, surgery or a combination thereof.

2. BACKGROUND

The success of cisplatin [cis-diamminedichloroplatinum (II)] to treat cancer has stimulated scientists to develop cisplatin analogues [Wong, E. et al. *Chem. Rev.* 1999, 99, 2451] and other classes of metal-based drug [Sadler, P. J. et al. *J. Am. Chem. Soc.* 2002, 124, 3064; Sadler, P. J. *Curr. Opin. Chem. Biol.* 2008, 12, 197]. A variety of gold(I) and gold(III) compounds have been demonstrated to overcome the cisplatin-related resistance and induce DNA-independent apoptosis [Berners-Price, S. J. (2011) Gold-Based Therapeutic Agents: A New Perspective, in Bioinorganic Medicinal Chemistry (ed E. Alessio), Wiley-VCH Verlag GmbH & Co. KGaA, Weinheim, Germany. doi:10.1002/9783527633104.ch7]. Nevertheless, one of the major challenges to clinically develop gold compounds as anti-cancer agents is to overcome the stability problem. Various reported gold(III) compounds are unstable under physiological conditions especially in the presence of biological reductants (e.g., glutathione). On the other hand, numerous reported gold(I) compounds would undergo rapid ligand exchanging reaction with physiological thiols (e.g., free cysteine in serum albumin) before reaching solid tumor tissues. As a consequence, the gold(I) compounds, such as auranofin, were found to be only effective to leukemia but display no effects to other solid tumors [Christopher et al. *Cancer Res.* 1985, 45, 32].

In literature, several physiological stable mono-nuclear gold(I) compounds which are relatively stable against ligand exchanging reactions with physiological thiols have been reported. One of these examples, [Au(dppe)$_2$]Cl (wherein dppe=1,2-bis(diphenylphosphino)ethane), which is a phosphine-containing gold(I) compound, was found to be inert to physiological thiols and can effectively inhibit tumor growth in vivo [Berners-Price, S. J. et al. *Cancer Res.* 1986, 46, 5486]. Yet, this compound displayed severe side effects and toxicity to lung, heart and liver, as a result of mitochondria dysfunction [Berners-Price, S. J.; Filipovska, A. *Metallomics* 2011, 3, 863]. In a recent study, another anti-cancer gold(I) compound [Au(d2pypp)$_2$]Cl (wherein d2pypp=1,3-bis(dipyridin-2-ylphosphino)propane) has been developed. This compound is relatively less lipophilic and has an increased reactivity towards thiol and may target to mitochondria thioredoxin reductase (TrxR). A cell-based study revealed that [Au(d2pypp)$_2$]Cl could selectively induce apoptosis in cancer cells but not in normal cells [Berners-Price, S. J. et al. *Dalton Trans* 2007, 4943]. We reckon that the anti-cancer activity as well as its bio-availability of this compound could be further enhanced by appropriate structural modification of the phosphine ligand. Nevertheless, there remains a formidable challenge for chemists to strategically modify this phosphine-containing compound, since modification on phosphine is rather complicated and it commonly requires Schlenk techniques and low-temperature (−40° C.) synthesis.

A series of binuclear gold(I) compounds [Au$_2$(dcpm)$_2$]$^{2+}$ (wherein dcpm=bis(dicyclohexylphosphanyl)methane) were found to be highly luminescent as a result from the Au(I) . . . Au(I) attraction (Che, C.-M. et al. *Angew. Chem. Int. Ed.* 1999, 38, 2783.; Che, C.-M. et al. *J. Am. Chem. Soc.* 1999, 121, 4799). Some binuclear gold(I) compounds such as [Au$_2$(dppm)Cl$_2$] (wherein dppm=bis(diphenylphosphino)methane) were found to induce autophagy in cancer cells (Che, C.-M. et al. *Chem. Commun.* 2011, 47, 9318). In addition to the phosphine ligands, N-heterocyclic carbene (NHC) and dithiocarbamate ligands have been employed to stabilize various kinds of metal ions in preparing metal-based anti-cancer agents (Che, C.-M. et al. *Chem. Commun.* 2010, 46, 3893; Che, C.-M. et al. *Chem. Sci.* 2011, 2, 728; Berners-Price, S. J.; Filipovska, A. et al. *J. Am. Chem. Soc.* 2008, 130, 12570; Fregona, D. et al. *Int. J. Cancer.* 2011, 129, 487). With these successful anti-cancer precedents, we believe that gold (I) compounds containing two different types of bidentate ligands including the diphosphine and dicarbene/dithiocarbamate would have potent prospects for the treatment of cancers.

3. SUMMARY

Described herein is a method of treating cancer by administering binuclear gold (I) compounds to a patient in need thereof. Binuclear gold(I) compounds are described hereinafter. By treatment, it is meant the induction of cell death, inhibition of cellular proliferation, inhibition of thioredoxin reductase (TrxR) activity, and inhibition of tumor growth in vivo. The amount of the binuclear gold(I) compound administered is an effective amount of the binuclear gold(I) compound for therapeutically treating the foregoing anti-cancer activities. The effective amount of the gold(I) compounds is dependent on the type and location of the cancer.

Described herein is a method of using binuclear gold(I) compounds (or gold(I) complex) for cancer treatment.

In one embodiment, a method for cancer treatment resulting in induction of cell death, inhibition of cellular proliferation, inhibition of thioredoxin reductase (TrxR) activity, or inhibition of tumor growth in vivo comprises administering in need thereof a composition comprising an effective amount of a binuclear gold(I) compound. The binuclear gold(I) compound is a gold(I) compound described herein can be represented by the structural formula of I, or a pharmaceutically acceptable salt thereof,

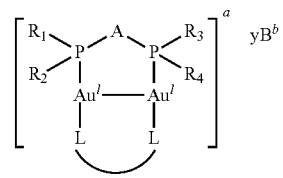

I

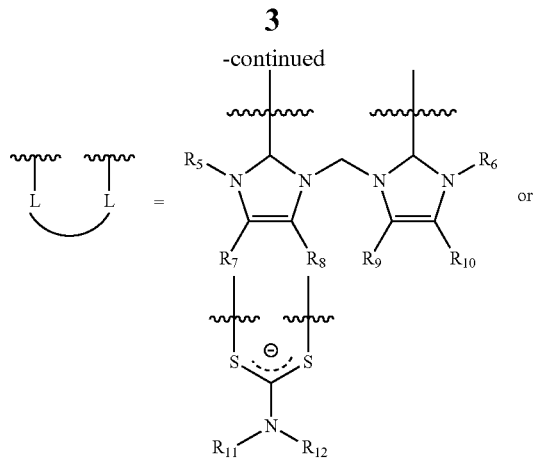

wherein, $R_1$, $R_2$, $R_3$, $R_4$ are each independently selected from cyclohexyl or phenyl ring;

$R_5$, $R_6$, $R_7$, $R_8$, $R_9$, $R_{10}$, $R_{11}$, $R_{12}$ are each independently selected from the group consisting of —H; —$CH_3$; —$C_2H_5$; —$C_4H_9$;

A is —$(CH_2)_m$—; m is an integer ranging from 1 to 3;

Each B is independently a pharmaceutically acceptable counter-ion;

a is an integer ranging from +1 to +2;

b is an integer ranging from −3 to −1;

y is equal to the absolute value of a/b.

The synthesis of these binuclear gold(I) compounds are preceded at room temperature with total yield up to 90%. These binuclear gold(I) compounds are stable in air and are less reactive towards physiological thiol. All of the described gold(I) compounds display higher anti-cancer activity than the clinically-used cisplatin. Using compound 1 as an example, this binuclear gold(I) compound displays promising anti-cancer activity in animal models.

4. BRIEF DESCRIPTION OF THE DRAWINGS

FIGS. 1A & B show (A) Chemical structures of binuclear gold(I) compounds; (B) Crystal structure of 1 (gold(I) . . . gold(I) distance: 3.083 Å).

Figure 2:
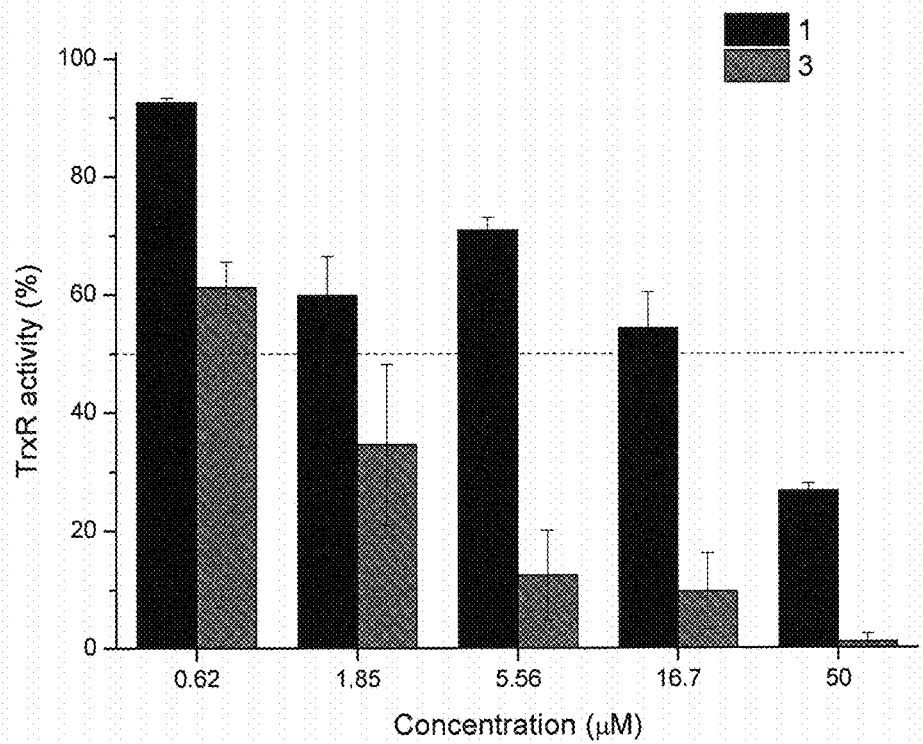

FIG. 2 shows cell based TrxR activity after treating HeLa cells with 1 and 3 for 1 h.

FIGS. 3A-C show (A) Graphical representation of tumor volumes (i) and body weight (ii) of HeLa xenograft-nude mouse models after treating with 5 mg/kg of 1 or solvent; (B & C) Representative photos of mice in different groups.

Figure 4:
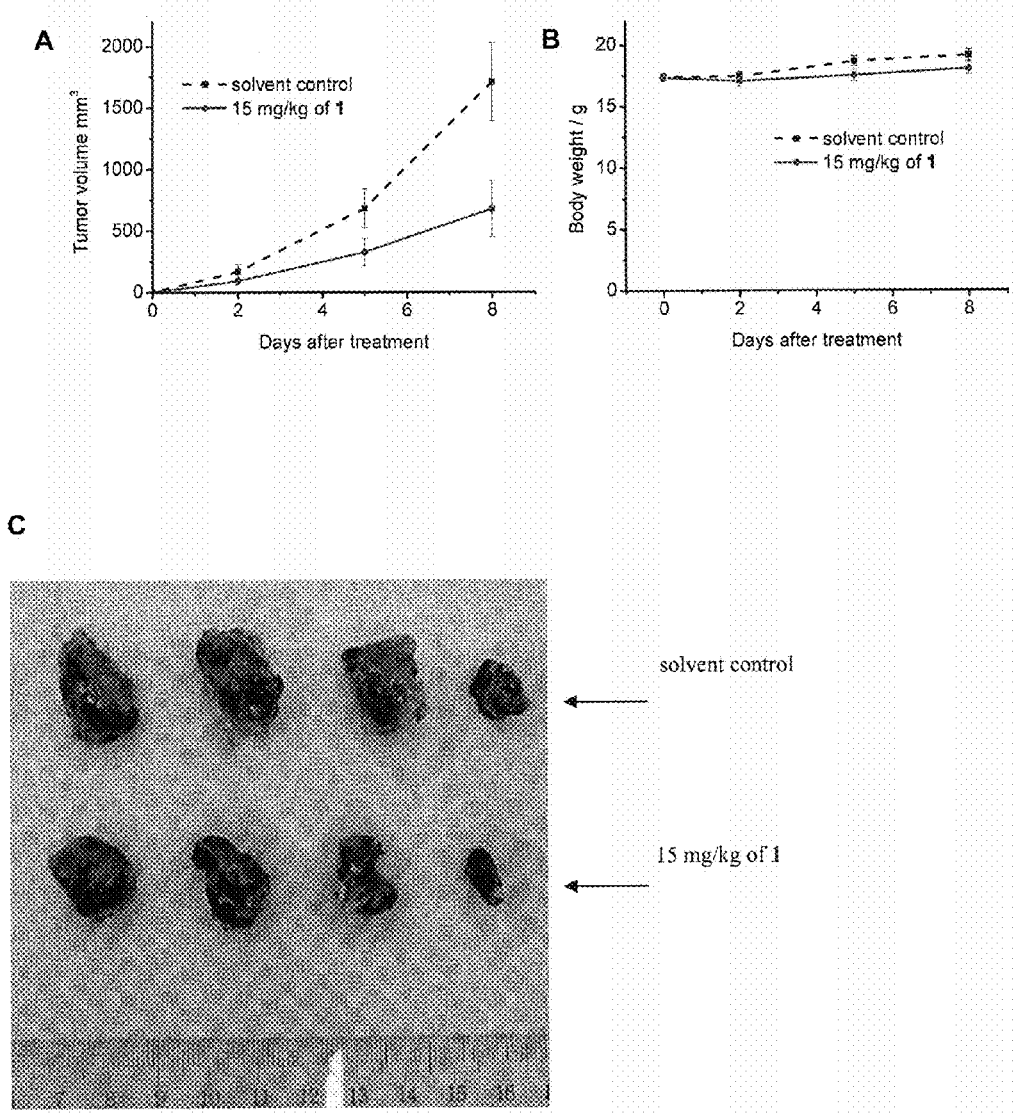

FIGS. 4A-C show (A) Graphical representation of tumor volumes; (B) Graphical representation of body weight of mouse B16-F10 melanoma model after treating with 15 mg/kg of 1 or solvent; (C) Representative photos of mice tumor in different groups.

Figure 5:
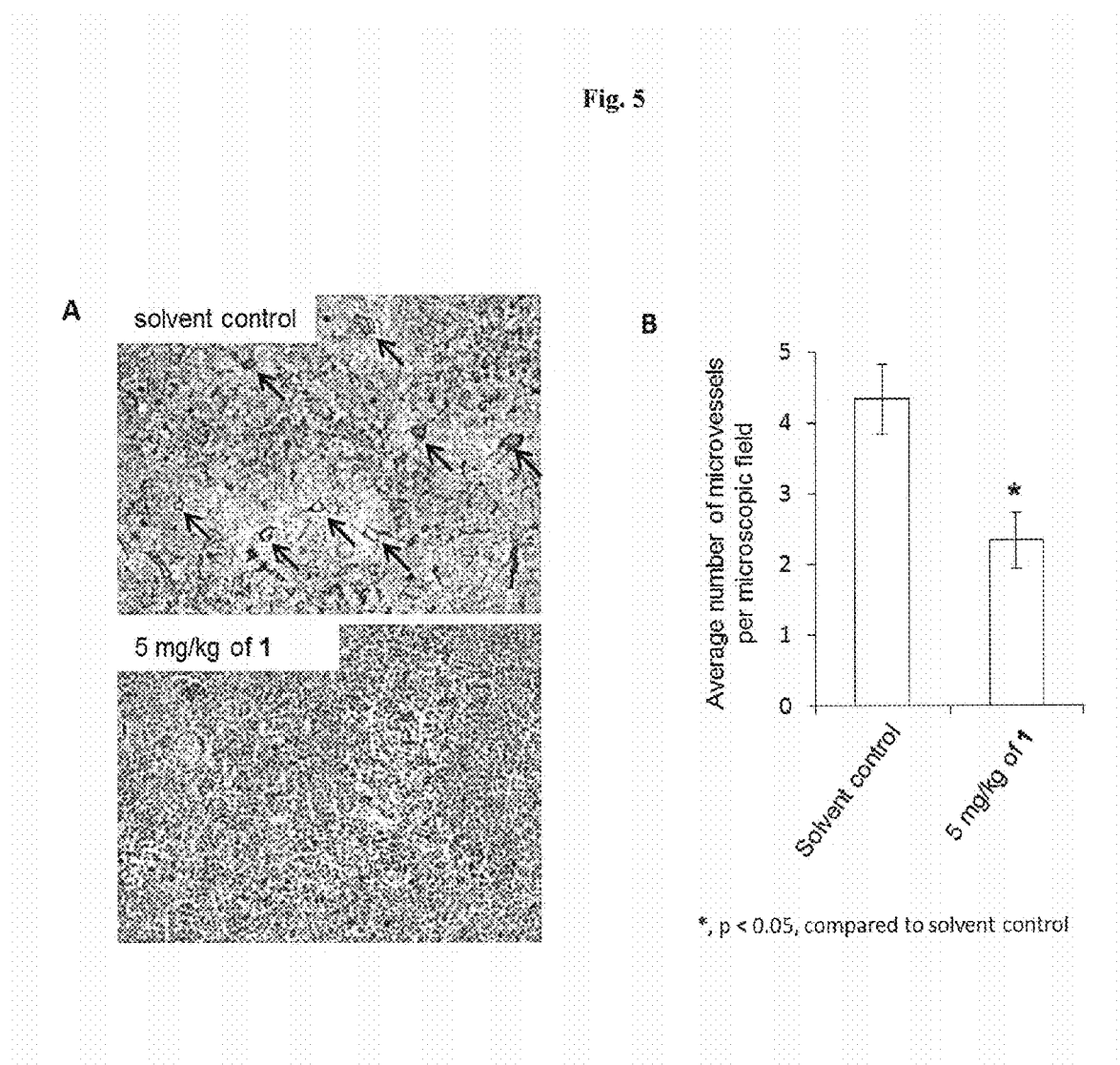

FIGS. 5A-B show (A) Immunohistochemical detection of CD31 in the tumor tissues of mice bearing HeLa xenograft after treating with 5 mg/kg of 1 or solvent. Arrows point to CD31-positive microvessels; (B) Graphical representation of the average number of microvessels per microscopic field.

FIGS. 6A-C show stability tests: (A) UV/vis absorption of 1 in PBS (containing 5% acetonitrile, v/v) at different time point; (B) Linear response of ESI-MS intensity of 1 versus concentration; (C) Kinetics analysis of reaction of 1 with GSH, auranofin was used as a reference compound. Unreacted compound percentage was calculated by combined MS intensity of each 10 scans at different time point then divided by pre-determined MS intensity of initial concentration.

5. DETAILED DESCRIPTION

Disclosed are the pharmaceutical binuclear gold(I) compounds, and the method of using these compounds for cancer treatment. Cancer treatment means a pharmaceutical composition containing at least one binuclear gold(I) compound in amount effective for an anti-cancer activity such as the induction of cell death, inhibition of cellular proliferation, inhibition of thioredoxin reductase (TrxR) activity, inhibition of tumor growth in vivo. As noted herein, "binuclear gold(I) compound" refers to a molecule containing two gold(I) ions and each gold(I) ion is connected to two bidentate ligands, which can be represented by structural formula I, or an acceptable salt thereof:

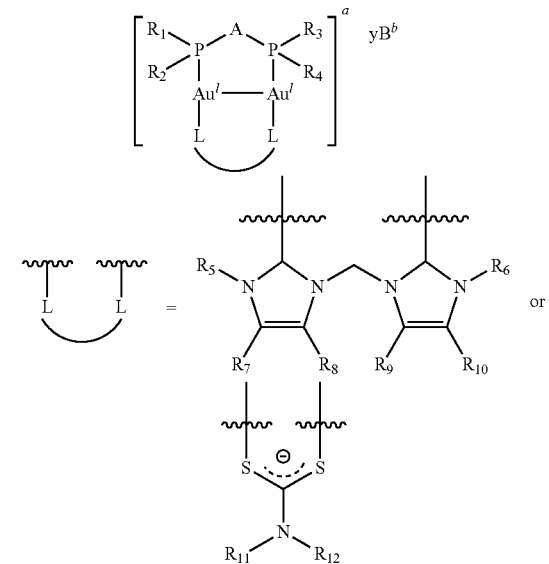

wherein, $R_1$, $R_2$, $R_3$, $R_4$ are each independently selected from cyclohexyl or phenyl ring;

$R_5$, $R_6$, $R_7$, $R_8$, $R_9$, $R_{10}$, $R_{11}$, $R_{12}$ are each independently selected from the group consisting of —H; —$CH_3$; —$C_2H_5$; —$C_4H_9$;

A is —$(CH_2)_m$—; m is an integer ranging from 1 to 3;

Each B is independently a pharmaceutically acceptable counter-ion;

a is an integer ranging from +1 to +2;

b is an integer ranging from −3 to −1;

y is equal to the absolute value of a/b.

As used herein, the term "bidentate ligand" refers to one ligand which has two donor atoms. Non-limiting examples of the bidentate ligands are:

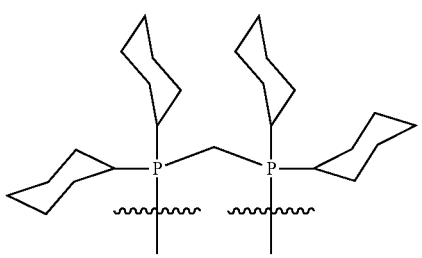

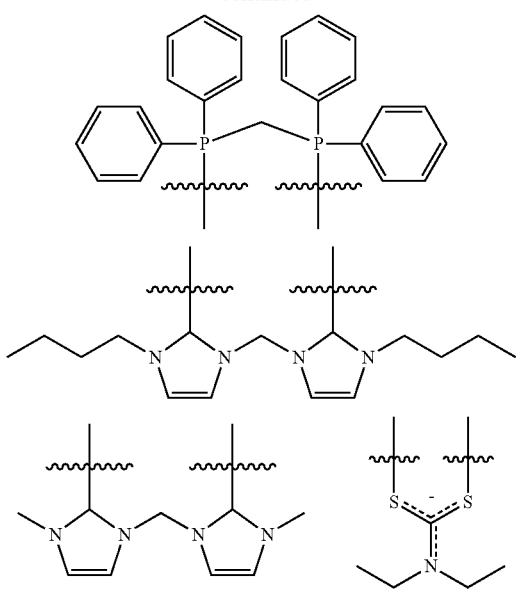

As used herein, the phrase "counter-anion" refers to an anion associated with a positively charged binuclear gold(I) compound. Non-limiting examples of counter-ions include halogens such as fluoride, chloride, bromide, iodide; sulfate; phosphate; trifluoromethanesulfonate; acetate; nitrate; perchlorate; acetylacetonate; hexafluorophosphate and hexafluoroacetylacetonate.

In one embodiment, the invention relates to a pharmaceutical composition for treatment of cancer by induction of cell death, inhibition of cellular proliferation, inhibition of TrxR activity, inhibition of tumor growth in vivo comprising an effective amount of a binuclear gold(I) compounds. Binuclear gold(I) compounds have a formula I or a pharmaceutically acceptable salt thereof, wherein,

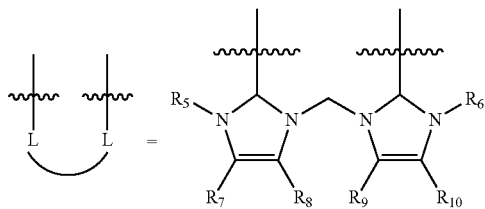

$R_1$, $R_2$, $R_3$ and $R_4$ are each cyclohexyl;
$R_5$, $R_6$ are each —$C_4H_9$;
$R_7$, $R_8$, $R_9$, $R_{10}$ are each —H;
A is —$CH_2$—;
a is +2, and
$yB^b$ is 2 $PF_6^-$ (compound 1)

In another embodiment, the invention relates to a pharmaceutical composition for treatment of cancer by induction of cell death, inhibition of cellular proliferation, inhibition of TrxR activity, inhibition of tumor growth in vivo comprising an effective amount of a binuclear gold(I) compound. Binuclear gold(I) compounds have a formula I or a pharmaceutically acceptable salt thereof, wherein,

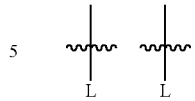 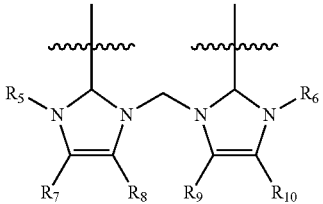

$R_1$, $R_2$, $R_3$ and $R_4$ are each cyclohexyl;
$R_5$, $R_6$ are each —$CH_3$;
$R_7$, $R_8$, $R_9$, $R_{10}$ are each —H;
A is —$CH_2$—;
a is +2, and
$yB^b$ is 2 $PF_6^-$ (compound 2)

In another embodiment, the invention relates to a pharmaceutical composition for treatment of cancer by induction of cell death, inhibition of cellular proliferation, inhibition of TrxR activity, inhibition of tumor growth in vivo comprising an effective amount of a binuclear gold(I) compounds. Binuclear gold(I) compounds have a formula I or a pharmaceutically acceptable salt thereof, wherein,

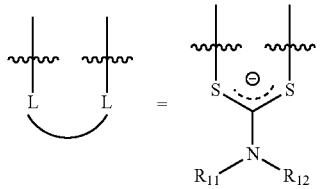

$R_1$, $R_2$, $R_3$ and $R_4$ are each cyclohexyl;
$R_{11}$, $R_{12}$ are each —$C_2H_5$;
A is —$CH_2$—;
a is +1, and
$yB^b$ is OTf⁻ (compound 3)

In another embodiment, the invention relates to a pharmaceutical composition for treatment of cancer by induction of cell death, inhibition of cellular proliferation, inhibition of TrxR activity, inhibition of tumor growth in vivo comprising an effective amount of a binuclear gold(I) compounds. Binuclear gold(I) compounds have a formula I or a pharmaceutically acceptable salt thereof, wherein, $R_1$, $R_2$, $R_3$ and $R_4$ are each phenyl;
$R_{11}$, $R_{12}$ are each —$C_2H_5$;
A is —$CH_2$—;
a is +1, and
$yB^b$ is OTf⁻. (compound 4)

5.1 Human Treatment

5.1.1 Formulations

The dinuclear gold(I) compounds provided herein can be administered to a patient in the conventional form of preparations such as injections. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the dinuclear gold(I) compounds provided herein in the pharmaceutical composition may be at a level that will exercise the desired effect.

In another embodiment, provided herein are compositions comprising an effective amount of dinuclear gold(I) compounds provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the dinuclear gold(I) compounds provided herein with a suitable carrier or diluent and filling the proper amount of the mixture in capsules.

5.2 Method of Use

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of dinuclear gold(I) compounds as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of dinuclear gold(I) compounds as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of dinuclear gold(I) compounds as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of dinuclear gold(I) compounds, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of dinuclear gold(I) compounds, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of dinuclear gold(I) compounds, as assessed by methods well known in the art, e.g., PET scan.

5.3 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered dinuclear gold(I) compounds or a pharmaceutical composition thereof, or a combination therapy before any adverse effects or intolerance to therapies other than the dinuclear gold(I) compounds develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with dinuclear gold(I) compounds, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

5.4 Dosage

In one aspect, a method for treating cancer presented herein involves the administration of a unit dosage of dinuclear gold(I) compounds thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of dinuclear gold(I) compounds that can be determined by one skilled in the art.

In some embodiments, a unit dose of dinuclear gold(I) compounds or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

5.5 Combination Therapy

Presented herein are combination therapies for the treatment of cancer which involve the administration of dinuclear gold(I) compounds in combination with one or more additional therapies to a subject in need thereof. In a specific embodiment, presented herein are combination therapies for the treatment of cancer which involve the administration of an effective amount of dinuclear gold(I) compounds in combination with an effective amount of another therapy to a subject in need thereof.

As used herein, the term "in combination," refers, in the context of the administration of dinuclear gold(I) compounds, to the administration of dinuclear gold(I) compounds prior to, concurrently with, or subsequent to the administration of one or more additional therapies (e.g., agents, surgery, or radiation) for use in treating cancer. The use of the term "in combination" does not restrict the order in which dinuclear gold (I) compounds and one or more additional therapies are administered to a subject. In specific embodiments, the interval of time between the administration of dinuclear gold(I) compounds and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, dinuclear gold(I) compounds and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering dinuclear gold(I) compounds daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, dinuclear gold(I) compounds and one or more additional therapies are cyclically administered to a subject. Cycling therapy involves the administration of dinuclear gold(I) compounds for a period of time, followed by the administration of one or more additional therapies for a period of time, and repeating this sequential administration. In certain embodiments, cycling therapy may also include a period of rest where dinuclear gold(I) compounds or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering dinuclear gold(I) compounds as a single agent for a period of time prior to administering the dinuclear gold(I) compounds in combination with an additional therapy. In certain embodiments, the methods for treating cancer provided herein comprise administering an additional therapy alone for a period of time prior to administering dinuclear gold(I) compounds in combination with the additional therapy.

In some embodiments, the administration of dinuclear gold (I) compounds and one or more additional therapies in accordance with the methods presented herein have an additive effect relative the administration of dinuclear gold(I) compounds or said one or more additional therapies alone. In some embodiments, the administration of dinuclear gold(I) compounds and one or more additional therapies in accordance with the methods presented herein have a synergistic effect relative to the administration of the Compound or said one or more additional therapies alone.

As used herein, the term "synergistic," refers to the effect of the administration of dinuclear gold(I) compounds in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of dinuclear gold(I) compounds or an additional therapy and/or less frequent administration of dinuclear gold(I) compounds or an additional therapy to a subject. In certain embodiments, the ability to utilize lower dosages of dinuclear gold(I) compounds or of an additional therapy and/or to administer dinuclear gold(I) compounds or said additional therapy less frequently reduces the toxicity associated with the administration of dinuclear gold(I) compounds or of said additional therapy, respectively, to a subject without reducing the efficacy of dinuclear gold(I) compounds or of said additional therapy, respectively, in the treatment of cancer. In some embodiments, a synergistic effect results in improved efficacy of dinuclear gold(I) compounds and each of said additional therapies in treating cancer. In some embodiments, a synergistic effect of a combination of dinuclear gold(I) compounds and one or more additional therapies avoids or reduces adverse or unwanted side effects associated with the use of any single therapy.

The combination of dinuclear gold(I) compounds and one or more additional therapies can be administered to a subject in the same pharmaceutical composition. Alternatively, dinuclear gold(I) compounds and one or more additional therapies can be administered concurrently to a subject in separate pharmaceutical compositions. Dinuclear gold(I) compounds and one or more additional therapies can be administered sequentially to a subject in separate pharmaceutical compositions. Dinuclear gold(I) compounds and one or more additional therapies may also be administered to a subject by the same or different routes of administration.

The combination therapies provided herein involve administering to a subject to in need thereof dinuclear gold(I) compounds in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with dinuclear gold(I) compounds include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with dinuclear gold(I) compounds include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with dinuclear gold(I) compounds include microtubule disasssembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with gold(I) complexes dinuclear gold(I) compoundsterocyclic carbene ligand include:

(1) a statin such as lovostatin (e.g., branded/marketed as MEVACOR®);

(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;

(3) a farnesyltransferase inhibitor agent such as tipifarnib;

(4) an antifibrotic agent such as pirfenidone;

(5) a pegylated interferon such as PEG-interferon alfa-2b;

(6) a CNS stimulant such as methylphenidate (branded/marketed as RITALIN®);

(7) a HER-2 antagonist such as anti-HER-2 antibody (e.g., trastuzumab) and kinase inhibitor (e.g., lapatinib);

(8) an IGF-1 antagonist such as an anti-IGF-1 antibody (e.g., AVE1642 and IMC-A11) or an IGF-1 kinase inhibitor;

(9) EGFR/HER-1 antagonist such as an anti-EGFR antibody (e.g., cetuximab, panitumamab) or EGFR kinase inhibitor (e.g., erlotinib; gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;

(19) immune modulator such as lenalidomide, pomalidomide, or thalidomide;

(20) kinase (e.g., tyrosine kinase) inhibitor such as imatinib, dasatinib, erlotinib, nilotinib, gefitinib, sorafenib, sunitinib, lapatinib, or TG100801;

(21) non-steroidal anti-inflammatory agent such as celecoxib (branded/marketed as CELEBREX®);

(22) human granulocyte colony-stimulating factor (G-CSF) such as filgrastim (branded/marketed as NEUPOGEN®);

(23) folinic acid or leucovorin calcium;

(24) integrin antagonist such as an integrin α5β1-antagonist (e.g., JSM6427);

(25) nuclear factor kappa beta (NF-κβ) antagonist such as OT-551, which is also an anti-oxidant.

(26) hedgehog inhibitor such as CUR61414, cyclopamine, GDC-0449, and anti-hedgehog antibody;

(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;

(28) retinoid such as isotretinoin (e.g., branded/marketed as ACCUTANE®)

(29) hepatocyte growth factor/scatter factor (HGF/SF) antagonist such as HGF/SF monoclonal antibody (e.g., AMG 102)

(30) synthetic chemical such as antineoplaston;

(31) anti-diabetic such as rosaiglitazone (e.g., branded/marketed as AVANDIA®)

(32) antimalarial and amebicidal drug such as chloroquine (e.g., branded/marketed as ARALEN®);

(33) synthetic bradykinin such as RMP-7;

(34) platelet-derived growth factor receptor inhibitor such as SU-101;

(35) receptor tyrosine kinase inhibitors of Flk-1/KDR/VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy

EXAMPLES

Example 6.1

Preparation and Characterization of the Binuclear Gold(I) Compounds

Example 1 illustrates the synthesis and characterization of the binuclear gold(I) compounds.

In general, the synthesis of 1 involves two steps where heating and protection of the reactants from oxygen are NOT required. Products can be obtained within 24 h, with high total yield (>90%). Pure product can be obtained by simple recrystallization. The synthesis route can be described below:

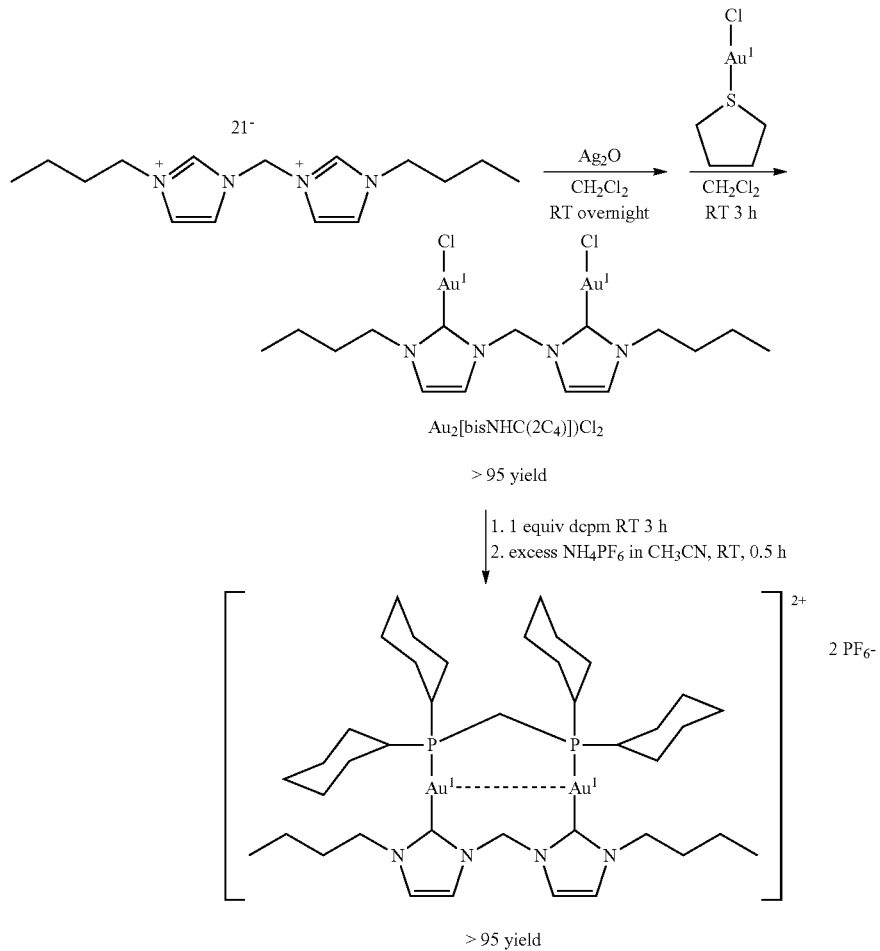

Details of the Synthesis

Compound 1 [Au$_2$-dcpm-bisNHC(2C4)](PF$_6$)$_2$

To a CH$_2$Cl$_2$ (10 mL) solution of Au$_2$-[bisNHC(2C$_4$)]Cl$_2$ (50 mg, 0.069 mmol) was added 28.2 mg of dcpm (0.069 mmol). After 3 h of stirring at room temperature, saturated 10 mL of NH$_4$PF$_6$ in CH$_3$CN were added and stirred for another 0.5 h. Then the mixture was evaporated, and solid was dissolved in water and extracted with CH$_2$Cl$_2$. After evaporating the organic layer and recrystallizing the solid, pure white solid was obtained after recrystallizing from hot ethanol. Crystal was obtained by diffusing diethyl ether into CH$_2$Cl$_2$/EtOH (2:1 v/v). Yield: 95%. $^1$H NMR (400M, MeOD, 298 K): 7.78 (d, 2H, J=1.6 Hz), 7.49 (d, 2H, J=1.5 Hz), 7.06 (d, 1H, J=14.3 Hz), 6.23 (d, 1H, J=14.3 Hz), 4.25 (m, 4H), 1.36-2.60 (m, 52H), 0.97 (t, 6H, J=7.4; H). $^{31}$P NMR (400M, MeOD, 298 K): 50.12. MS-FAB(+): 1061 (M-2 PF$_6$-1), 1207 (M-PF$_6$), 531 ([M-2 PF$_6$]/2). Elemental Analysis: calcd: C, 35.51; H, 5.22; N, 4.14. found: C, 35.21; H, 5.23; N, 4.19.

Compound 2 [Au$_2$-dcpm-bisNHC(2Me)] (PF$_6$)$_2$

The synthesis was similar to compound 1. Yield: 60%. $^1$H NMR (300M, MeOD, 298 K): 7.76 (d, 2H, J=2.2 Hz), 7.44 (d, 2H, J=2.3 Hz), 6.74 (d, 1H, J=18.8 Hz), 6.28 (d, 1H, J=19.2 Hz), 3.94 (s, 4H), 3.1-2.8 (m, 2H), 2.72 (m, 2H), 2.7-1.2 (m, 36H), 0.97 (t, 6H, J=7.4; H).

Compound 3 [Au$_2$-dcpm-dedt] (OTf)

To an acetone (10 mL) solution of Au$_2$(dcpm)Cl$_2$ (50 mg, 0.057 mmol) was added 19.4 mg of sodium diethylcarbamodithioate (Et$_2$NCS$_2$Na 3H$_2$O, 0.086 mmol, 1.5 equiv). After stirring at room temperature overnight, the mixture was evaporated and washed with water. Then the solid was redissolved in CH$_3$CN, followed by the addition of excess of lithium trifluoromethanesulfonate (LiOTf) and stirred for another 0.5 h at room temperature. Then the solution was evaporated and extracted with CH$_2$Cl$_2$, and recrystallized with CH$_2$Cl$_2$/Et$_2$O. White yellow solid was obtained. Yield: 60%. $^1$H NMR (400M, CDCl$_3$, 298 K): 3.94 (q, 4H, J=1.6 Hz), 2.61 (t, 2H, J=10.9 Hz), 2.26 (m, 4H), 2.02 (m, 8H), 1.90 (m, 8H), 1.74 (m, 4H), 1.52-1.20 (m, 26H)

Compound 4 [Au$_2$-dppm-dedt] (OTf)

Compound 4 was synthesized similar to compound 3. White yellow solid was obtained. Yield: 60%. $^1$H NMR (400M, CDCl$_3$, 298 K): 7.65 (m, 8H), 7.32 (m, 12H), 3.99 (q, 4H, J=10.9 Hz), 3.86 (t, 2H, J=12.2 Hz), 1.41 (t, 6H, J=7.1 Hz)

Example 6.2

In Vitro Cytotoxicity of the Binuclear Gold(I) Compounds

Example 2 describes the in vitro cytotoxicity, which is indicative of the induction of cell death and/or inhibition of cellular proliferation of cancer cells, of the binuclear gold(I) compounds on cervical epithelioid carcinoma, lung carcinoma, hepatocellular carcinoma, and breast carcinoma.

By means of MTT assays, the cytotoxic properties of binuclear gold(I) compounds (1-4) were determined toward some established human cancer cell lines including cervical epithelioid carcinoma (HeLa), lung carcinoma (H1950, HCC827), hepatocellular carcinoma (HepG2), breast carcinoma (MCF-7), and human nasopharyngeal carcinoma (HONE1, SUNE1).

The IC$_{50}$ values (dose required to inhibit 50% cellular growth for 72 h) of the binuclear gold(I) compounds are listed in Table 1. All the binuclear gold(I) compounds exhibit promising cytotoxicity toward these cell lines. In terms of the IC$_{50}$ values, they display similar cytotoxic properties compared to the reference compound cisplatin.

TABLE 1

Cytotoxicity IC$_{50}$ values (μM, 72 h of incubation) of binuclear gold(I) compounds to selected human cancer cell lines

| compound | HeLa | HepG2 | MCF-7 | HONE1 | SUNE1 | H1975 | HCC827 |
|---|---|---|---|---|---|---|---|
| 1 | 2.44 ± 0.15 | 13.8 ± 0.8 | 2.50 ± 0.37 | 1.04 ± 0.03 | 1.33 ± 0.21 | 1.39 ± 0.07 | 5.41 ± 0.46 |
| 2 | 1.66 ± 0.21 | 14.5 ± 4.3 | 4.17 ± 0.18 | 0.55 ± 0.03 | 1.09 ± 0.24 | 1.11 ± 0.09 | 4.42 ± 1.70 |
| 3 | <0.39 | 0.54 ± 0.07 | 0.41 ± 0.20 | 0.41 ± 0.07 | 0.67 ± 0.28 | — | — |
| 4 | 0.63 | 0.95 ± 0.58 | 0.50 ± 0.06 | 0.59 ± 0.04 | 1.62 ± 0.44 | <0.19 | 0.48 ± 0.06 |
| Cisplatin | 6.64 ± 1.09 | 79.8 ± 5.3 | 33.7 ± 7.8 | 2.23 ± 0.42 | 9.59 ± 5.26 | 18.0 ± 4.4 | 27.5 |

Example 6.3

Reactivity Towards Physiological Thiols

Example 3 describes the results of reactivity towards physiological thiols.

It was believed that high reactivity of the gold(I) anticancer drugs towards physiological thiols may fail the drugs targeting to the solid tumor tissue thus hamper the application for in vivo cancer treatment. As a result, high resolution ESI-MS was applied to monitor the reaction of 1 with thiol-containing GSH.

Figure 6:
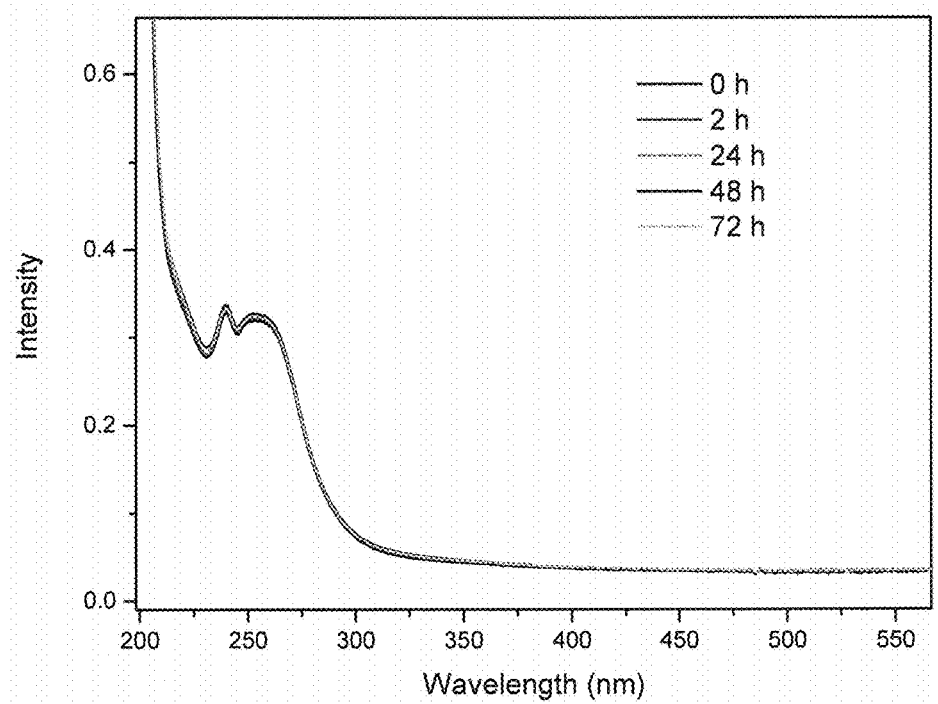
Figure 6:
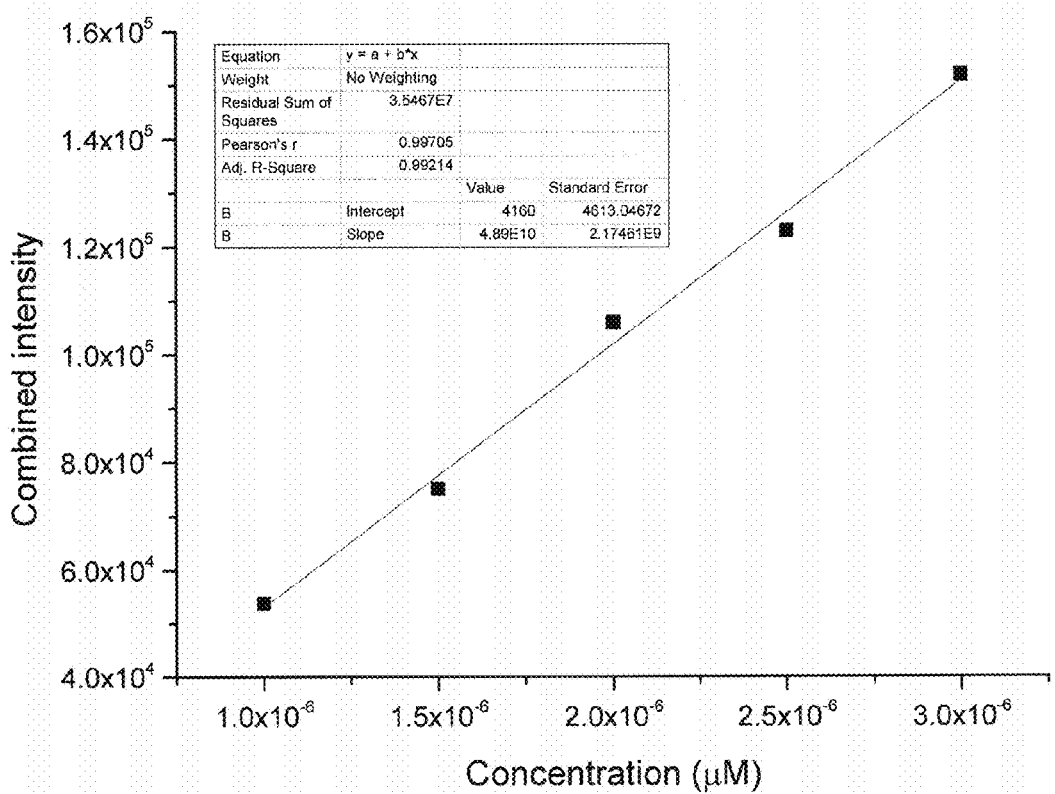
Figure 6:
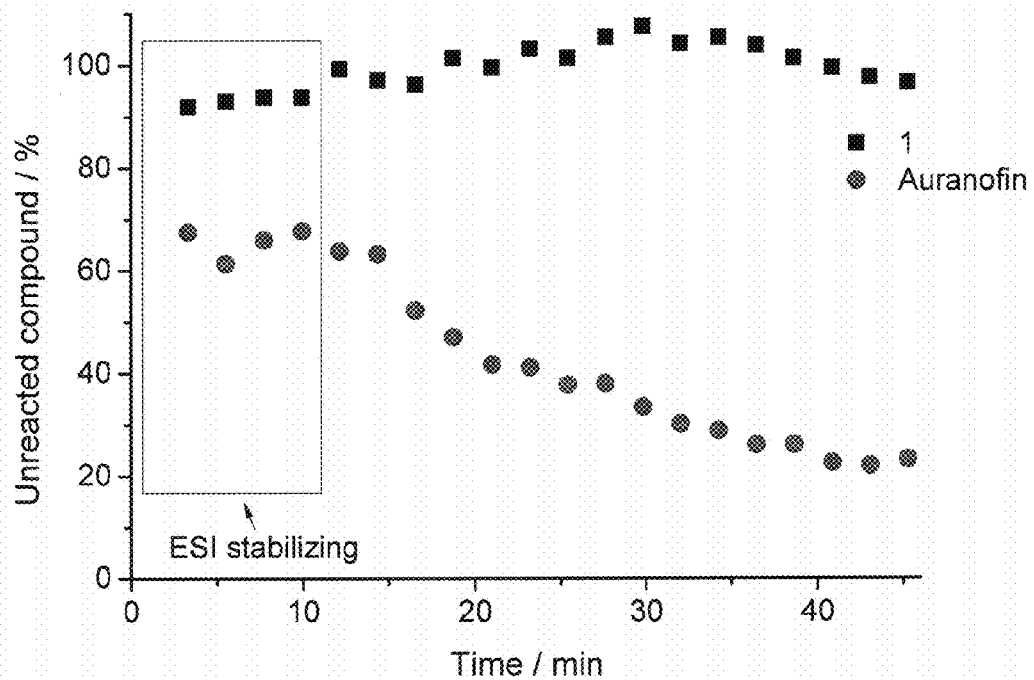

Firstly, MS intensity at different concentrations of 1 was recorded to find the linear response of MS intensity against concentration, and results show that 1 has a linear intensity response against concentration at $1\times10^{-6}$M to $3\times10^{-6}$M (FIG. 6). Then initial concentration of $3\times10^{-6}$M of 1 with $1.5\times10^{-5}$M or $5\times10^{-5}$M of GSH was used and the intensity of 1 or auranofin (reference compound) was measured every 1 s for about 45 min Results revealed that, for the reaction of 1 with GSH, the intensity was not significantly changed after 45 min (FIG. 6); indicating 1 has little reaction towards GSH at this concentrations. If higher concentration of GSH ($5\times10^{-5}$ M) was used, 1 also has little effects towards GSH. As a comparison, for the reaction of auranofin, a clinical used anti-rheumatic agent which has good in vitro anti-cancer effects but has no effects to solid tumors, with GSH, auranofin has a fast reaction towards GSH (see FIG. 6 for details).

Example 6.4

Cell Based Thioredoxin Reductase Activities

Example 4 describes the results of cell based thioredoxin reductase activities.

It was reported that thiol/selenol containing proteins, like thioredoxin reductase (TrxR), were the major targets for gold (I) based anticancer agents. As a result, cell based TrxR were tested for all the compounds.

In general, cells were seeded at $2\times10^5$/well in 6-well plates and incubated for 24 h. Compounds were serially diluted and added to the cells (final DMSO concentrations ≤1%). After incubation for 1, 3, 6 and 9 h, the cells were washed three times with PBS, and 100 μl of ice-cold lysis buffer (50 mM phosphate buffer, pH 7.4, 1 mM EDTA, 0.1% Triton-X 100) were added to the cell layer. Cell lysis was carried on ice for 5 mM and the cell lysates were collected and stored at −80° C. or assayed immediately.

Figure 3:
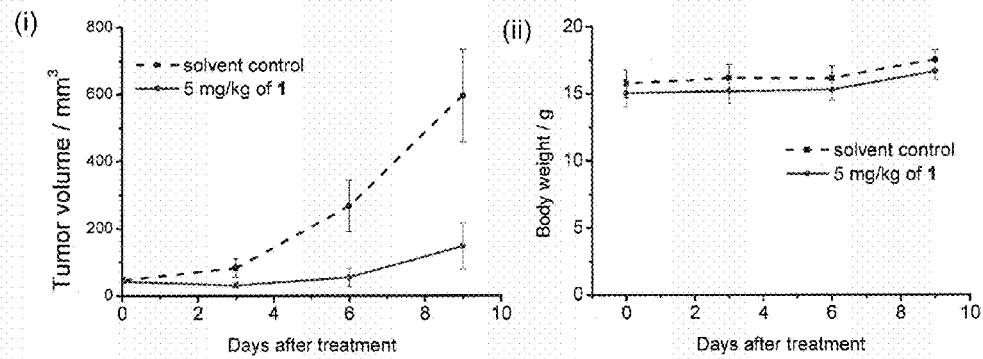
Figure 3:
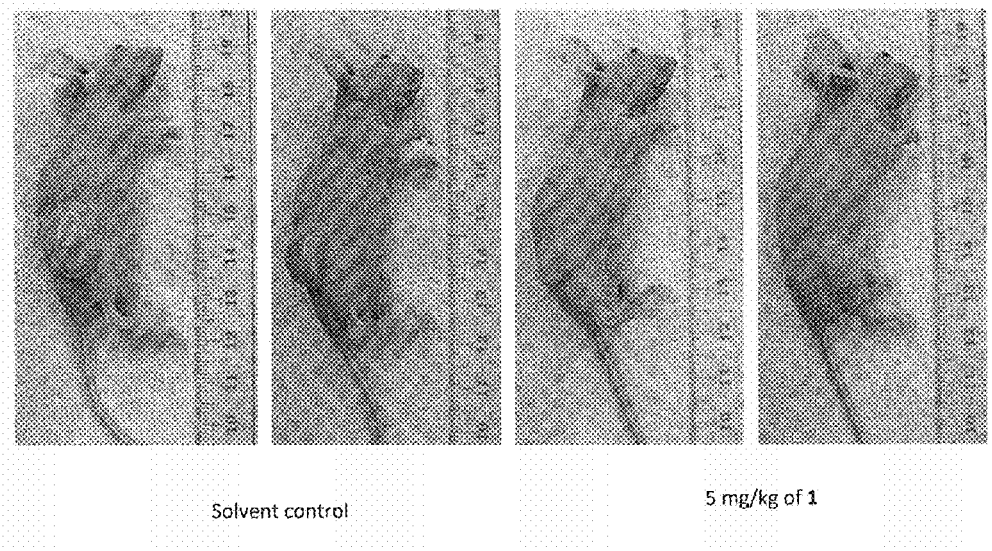
Figure 3:
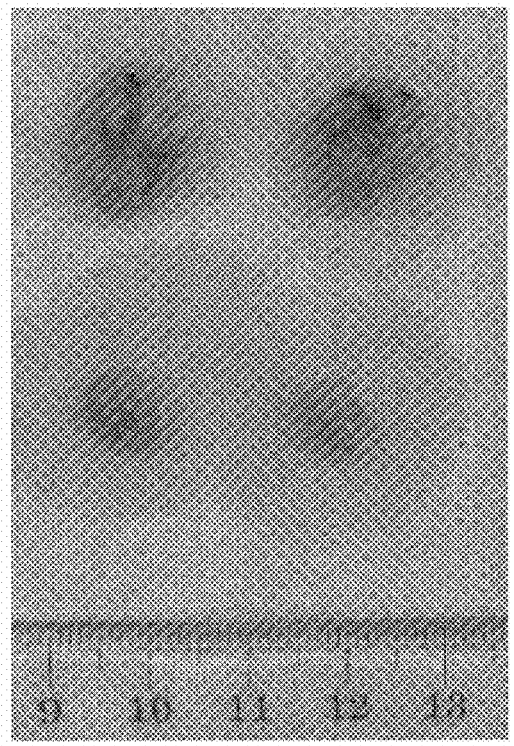

Cell lysates (10 μg proteins) were added to a buffer (100 μl) containing 50 mM potassium phosphate, pH 7.4, 1 mM EDTA and 0.2 mM NADPH. 5 minutes later, reaction was initiated by adding 5,5'-dithiobis(2-nitrobenzoic acid) (DTNB, 3 mM final) and the TrxR activities were determined as increases in O.D.$_{412\,nm}$ in 10-15 min Results show that treatment of HeLa cells with 1 for 1, 3, 6 and 9 h resulted in the TrxR activity inhibition IC$_{50}$ of the cell lysates of 29.3, 18.7, 16.6 and 10.5 μM, respectively. And this is consistent with the time dependent cytotoxicity IC$_{50}$ values of 9.66 μM for 24 h, 3.96 μM for 48 h, and 2.44 μM for 72 h. The cellular TrxR inhibition of 1 h treatment of 1 and 3 is shown in FIG. 3.

Example 6.5

In Vivo Tumor Growth by Treating with the Binuclear Gold(I) Compounds

Example 5 describes the results of in vivo cytotoxicity study of compound 1.

Prompted by the prominent in vitro cytotoxicity and the low thiol reactivity towards physiological thiols, the in vivo anti-cancer property of compound 1 was preliminarily examined by using mice models with the approval from the committee on the Use of Live Animals for Teaching and Research (The University of Hong Kong).

Female BALB/cAnN-nu (Nude) and female C57BL/6 mice, 5-7 weeks old, were purchased from the Charles River Laboratories (Wilmington, Mass.) and cared for according to the guidelines of the Laboratory Animal Unit of the University of Hong Kong (HKU).

To establish the HeLa xenograft model, $4\times10^6$ HeLa cells suspended in 100 μl of PBS were inoculated into the back flanks of female BALB/cAnN-nu (Nude) mice by subcutaneous injection. When the tumor volumes reached about 50 mm³ (4 days after tumor inoculation), the mice were randomly divided into different treatment groups (5 mg/kg of 1 or solvent control). Complex 1 was reconstituted in PET diluent (60% polyethylene glycol 400, 30% ethanol, 10% Tween 80). Complex 1 dissolved in PET diluent and then diluted in PBS or PBS supplemented with equal amount of PET injected into the mice by intraperitoneal injection once every three days until the mice were sacrificed.

To establish the mouse melanoma model, $4\times10^5$ B16-F10 melanoma cells were inoculated into the right back flanks of female C57BL/6N mice by subcutaneous injection. Five days after tumor inoculation, the mice were randomly divided into different treatment groups (solvent control or 15 mg/kg of 1). Solvent control or 15 mg/kg of 1 dissolved in PET diluent and then diluted in PBS was injected into the mice by intraperitoneal injection once every 2-3 days until the mice were sacrificed. In both model, the volume of PET diluent injected into each mouse was 6 μl. Tumor sizes were measured once every 2-3 days, and tumor volume (V) was calculated by the formula $V=ab^2\times0.52$, where a and b were the longest and the shortest diameters of the xenografted tumor.

Tumor growth inhibition was calculated $[1-(V_{treatment}-V_0)/(V_{control}-V_0')]\times100\%$, where $V_{treatment}$ is the final tumor volume of the treatment group, $V_0$ is the initial volume of the treatment group. $V_{control}$ is the final tumor volume of the solvent control group, $V_0'$ is the initial volume of the solvent control group.

Results demonstrated that 81% inhibition of tumor growth in HeLa xenograft nude mouse model and 62% inhibition of tumor growth in B16-F10 melanoma mouse model. No mouse death or body weight loss was found for these two models.

Example 6.6

In Vivo Angiogenesis of the Binuclear Gold(I) Compounds

Example 6 describes the results of in vivo angiogenesis study of compound 1.

Immunohistochemical detection of CD31 in the tumor tissues of mice was incorporated in different treatment groups. Pictures shown were taken at 200× magnification. Ten fields were randomly chosen and the number of microvessels per field was counted.

Results showed the number of microvessels was significantly lower in mice treated with 1, compared to those treated with solvent control, indicating tumor growth was caused by inhibition of angiogenesis.

The dosage of gold (I) is a sufficient amount to inhibit tumor growth and may be dependent on the type of cancer and location of the cancer. This amount may be about 0.1 mg/kg to about 100 mg/kg for mice and humans. Intraperitoneal injection, intravenous injection or direct intratumoral injection of gold(I) drug is preferred. Many pharmaceutical dosage forms are available for administering the gold(I) compounds. Preferably, pharmaceutical dosage forms suitable for injection or infusion include sterile aqueous solutions or dispersions or sterile powders comprising gold(I) which are adapted for facile preparation of sterile injectable or infusible solutions or dispersions are utilized. In all cases, the dosage form should be sterile, fluid and stable under the conditions of manufacture and storage. The liquid carrier or vehicle can be a solvent or liquid dispersion medium comprising, for example, water, ethanol, a polyol, vegetable oil, nontoxic glyceryl esters and suitable mixtures thereof.

What is describe herein is merely illustrative of the binuclear gold(I) compounds and their activity. Other embodiments may be implemented by those skilled in the art without departing from the scope and spirit of the present invention.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of inhibiting thioredoxin reductase (TrxR) activity in a patient having cancer comprising administering an effective amount of a binuclear gold(I) compound to a patient in need thereof having a formula I, wherein,

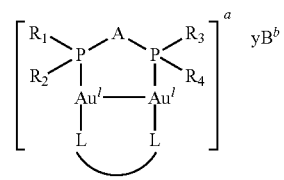

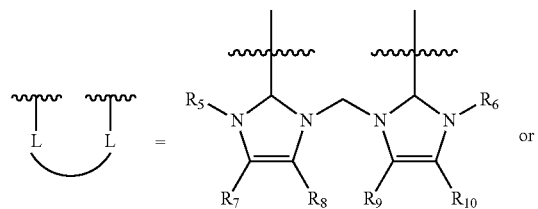

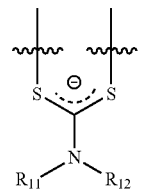

$R_1$, $R_2$, $R_3$, $R_4$ are each independently selected from cyclohexyl or phenyl ring;

$R_5$, $R_6$, $R_7$, $R_8$, $R_9$, $R_{10}$, $R_{11}$, $R_{12}$ are each independently selected from the group consisting of —H; —CH$_3$; —C$_2$H$_5$; —C$_4$H$_9$;

A is —(CH$_2$)$_m$—; m is an integer ranging from 1 to 3;

Each B is independently a pharmaceutically acceptable counter-ion;

a is an integer ranging from +1 to +2;

b is an integer ranging from −3 to −1;

y is equal to the absolute value of a/b.

2. The method of claim 1, wherein,

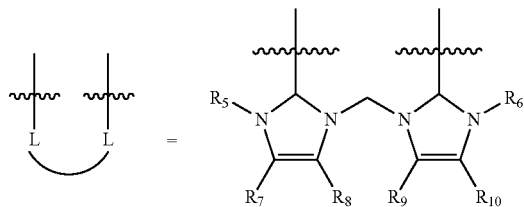

$R_1$, $R_2$, $R_3$ and $R_4$ are each cyclohexyl;
$R_5$, $R_6$ are each —$C_4H_9$;
$R_7$, $R_8$, $R_9$, $R_{10}$ are each —H;
A is —$CH_2$—;
a is +2, and
$yB^b$ is 2 $PF_6^-$ (compound 1).

3. The method of claim 1, wherein,

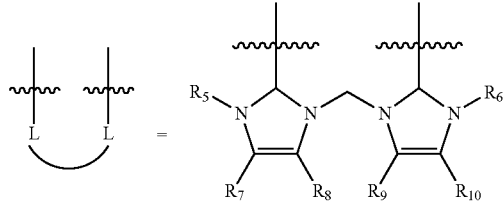

$R_1$, $R_2$, $R_3$ and $R_4$ are each cyclohexyl;
$R_5$, $R_6$ are each —$CH_3$;
$R_7$, $R_8$, $R_9$, $R_{10}$ are each —H;
A is —$CH_2$—;
a is +2, and
$yB^b$ is 2 $PF_6^-$ (compound 2).

4. The method of claim 1, wherein,

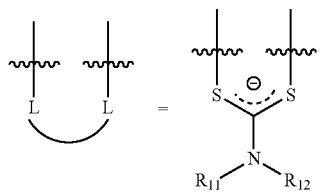

$R_1$, $R_2$, $R_3$ and $R_4$ are each cyclohexyl;
$R_{11}$, $R_{12}$ are each —$C_2H_5$;
A is —$CH_2$—;
a is +1, and
$yB^b$ is OTf⁻ (compound 3).

5. The method of claim 1, wherein,

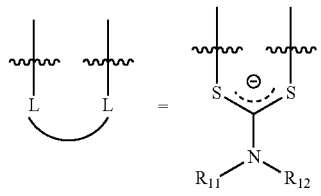

$R_1$, $R_2$, $R_3$ and $R_4$ are each phenyl;
$R_{11}$, $R_{12}$ are each —$C_2H_5$;
A is —$CH_2$—;
a is +1, and
$yB^b$ is OTf⁻ (compound 4).

6. The method of claim 1, wherein the cancer is one or more of cervical epithelioid carcinoma, lung carcinoma, hepatocellular carcinoma, breast carcinoma, melanoma.

7. The method of claim 1 wherein the preferred amount of the administration of the compound of formula I is about 0.1 mg/kg to about 100 mg/kg.

* * * * *